United States Patent
Young et al.

(10) Patent No.: US 7,572,266 B2
(45) Date of Patent: Aug. 11, 2009

(54) CLIP APPLIER TOOL HAVING A DISCHARGE CONFIGURATION

(76) Inventors: Wayne P. Young, 104 Allview Ave., Brewster, NY (US) 10509; Keith Ratcliff, 14 Concord Ridge Rd., Newtown, CT (US) 06470; George R. Trutza, 1 Foster Way, East Greenwich, RI (US) 02818

( * ) Notice: Subject to any disclaimer, the term of this patent is extended or adjusted under 35 U.S.C. 154(b) by 0 days.

(21) Appl. No.: 10/969,138

(22) Filed: Oct. 20, 2004

(65) Prior Publication Data

US 2005/0149063 A1 Jul. 7, 2005

Related U.S. Application Data

(60) Provisional application No. 60/513,518, filed on Oct. 21, 2003.

(51) Int. Cl.
 *A61B 17/10* (2006.01)
(52) U.S. Cl. ..................... 606/143; 606/151
(58) Field of Classification Search ................ 606/139, 606/142, 151, 157, 144, 219, 221
 See application file for complete search history.

(56) References Cited

U.S. PATENT DOCUMENTS

| | | |
|---|---|---|
| 648,841 A | 5/1900 | Brosnan |
| 1,332,287 A | 3/1920 | Genevieve et al. |
| 1,458,797 A | 6/1923 | Beale |
| 1,666,514 A | 4/1928 | Sigler |
| 2,113,991 A | 4/1938 | Larsen |
| 2,498,372 A | 2/1950 | Kortlucke, Jr. et al. |
| 2,626,608 A | 1/1953 | Garland |
| 2,874,384 A | 2/1959 | Krone |
| 2,876,778 A | 3/1959 | Kees, Jr. |
| 3,023,039 A | 2/1962 | Henningson et al. |
| 3,023,468 A | 3/1962 | Hord et al. |
| 3,032,039 A | 5/1962 | Beaty |
| 3,056,408 A | 10/1962 | Brown |
| 3,098,232 A | 7/1963 | Brown |
| 3,120,230 A | 2/1964 | Skold |
| 3,125,789 A | 3/1964 | Parker |
| 3,270,745 A | 9/1966 | Wood |

(Continued)

FOREIGN PATENT DOCUMENTS

DE 2 330 182 1/1975

(Continued)

OTHER PUBLICATIONS

Papainoannou, Thanassis, M.S., Daykhovsky, Leon, M.D., Grundfest, Warren S., M.D.: "Safety Evaluation of Laproscopically Applied Clips"; *Journal of Laproscopic Surgery* 1996: 6(2): 99-106.

(Continued)

*Primary Examiner*—Anhtuan T. Nguyen
*Assistant Examiner*—Tuan V Nguyen
(74) *Attorney, Agent, or Firm*—Martin & Ferraro, LLP

(57) ABSTRACT

A surgical ligation instrument and method for ligating a fluid carrying structure are provided. In one aspect, there is provided a surgical ligation instrument and method for deploying a spring clip over the fluid carrying structure without pre-clamping the fluid carrying structure.

26 Claims, 6 Drawing Sheets

U.S. PATENT DOCUMENTS

| | | |
|---|---|---|
| 3,274,658 A | 9/1966 | Pile |
| 3,363,628 A | 1/1968 | Wood |
| 3,439,522 A | 4/1969 | Wood |
| 3,439,523 A | 4/1969 | Wood |
| 3,476,114 A | 11/1969 | Shannon et al. |
| 3,518,993 A | 7/1970 | Blake |
| 3,631,707 A | 1/1972 | Miller |
| 3,675,688 A | 7/1972 | Bryan et al. |
| 3,683,927 A | 8/1972 | Noiles |
| 3,757,829 A | 9/1973 | Schneider |
| 3,777,538 A | 12/1973 | Weatherty et al. |
| 3,827,277 A | 8/1974 | Weston |
| 3,827,438 A | 8/1974 | Kees |
| 3,882,854 A | 5/1975 | Hulka et al. |
| 3,911,923 A | 10/1975 | Yoon |
| 3,955,581 A | 5/1976 | Spasiano et al. |
| 3,989,049 A | 11/1976 | Yoon |
| 4,017,337 A | 4/1977 | Winter et al. |
| 4,024,868 A | 5/1977 | Williams |
| 4,027,510 A | 6/1977 | Hiltebrandt |
| 4,038,987 A | 8/1977 | Komiya |
| 4,041,931 A | 8/1977 | Elliot et al. |
| 4,064,881 A | 12/1977 | Meredith |
| 4,086,926 A | 5/1978 | Green et al. |
| 4,146,130 A | 3/1979 | Samuels et al. |
| 4,152,920 A | 5/1979 | Green |
| 4,169,476 A | 10/1979 | Hiltebrandt |
| 4,170,990 A | 10/1979 | Baumgart et al. |
| 4,196,836 A | 4/1980 | Becht |
| 4,217,902 A | 8/1980 | March |
| 4,226,239 A | 10/1980 | Polk et al. |
| 4,226,242 A | 10/1980 | Jarvik |
| 4,228,895 A | 10/1980 | Larkin |
| 4,241,734 A | 12/1980 | Kandel et al. |
| 4,242,902 A | 1/1981 | Green |
| 4,246,903 A | 1/1981 | Larkin |
| 4,274,415 A | 6/1981 | Kanamoto et al. |
| 4,299,224 A | 11/1981 | Noiles |
| 4,317,451 A | 3/1982 | Cerwin et al. |
| 4,340,061 A | 7/1982 | Kees, Jr. et al. |
| 4,349,028 A | 9/1982 | Green |
| 4,367,746 A | 1/1983 | Derechinsky |
| 4,372,316 A | 2/1983 | Blake, III et al. |
| 4,374,523 A | 2/1983 | Yoon |
| 4,396,139 A | 8/1983 | Hall et al. |
| 4,412,539 A | 11/1983 | Jarvik |
| 4,418,694 A | 12/1983 | Beroff et al. |
| 4,425,915 A | 1/1984 | Ivanov |
| 4,427,008 A | 1/1984 | Transue |
| 4,430,997 A | 2/1984 | DiGiovanni et al. |
| 4,433,689 A | 2/1984 | von Zeppelin |
| 4,444,187 A | 4/1984 | Perlin |
| 4,448,193 A | 5/1984 | Ivanov |
| 4,449,530 A | 5/1984 | Bendel et al. |
| 4,450,839 A | 5/1984 | Transue |
| 4,450,840 A | 5/1984 | Mericle et al. |
| 4,471,766 A | 9/1984 | Terayama |
| 4,471,780 A | 9/1984 | Menges et al. |
| 4,476,865 A | 10/1984 | Failla et al. |
| 4,478,218 A | 10/1984 | Mericle |
| 4,478,220 A | 10/1984 | Di Giovanni et al. |
| 4,480,641 A | 11/1984 | Failla et al. |
| 4,485,816 A | 12/1984 | Krumme |
| 4,487,205 A | 12/1984 | Di Giovanni et al. |
| 4,492,232 A | 1/1985 | Green |
| 4,493,319 A | 1/1985 | Polk et al. |
| 4,500,024 A | 2/1985 | DiGiovanni et al. |
| 4,509,518 A | 4/1985 | McGarry et al. |
| 4,512,345 A | 4/1985 | Green |
| 4,527,562 A | 7/1985 | Mericle |
| 4,550,715 A | 11/1985 | Santangelo et al. |
| 4,556,058 A | 12/1985 | Green |
| 4,556,060 A | 12/1985 | Perlin |
| 4,557,263 A | 12/1985 | Green |
| 4,562,839 A | 1/1986 | Blake, III et al. |
| 4,569,346 A | 2/1986 | Poirier |
| 4,570,633 A | 2/1986 | Golden |
| 4,590,937 A | 5/1986 | Deniega |
| 4,616,650 A | 10/1986 | Green et al. |
| 4,616,651 A | 10/1986 | Golden |
| 4,620,541 A | 11/1986 | Gertzman et al. |
| 4,624,254 A | 11/1986 | McGarry et al. |
| 4,637,395 A | 1/1987 | Caspar et al. |
| 4,638,804 A | 1/1987 | Jewusiak |
| 4,646,741 A | 3/1987 | Smith |
| 4,658,822 A | 4/1987 | Kees, Jr. |
| 4,660,558 A | 4/1987 | Kees, Jr. |
| 4,662,373 A | 5/1987 | Montgomery et al. |
| 4,665,906 A | 5/1987 | Jervis |
| 4,671,278 A * | 6/1987 | Chin .......................... 606/143 |
| 4,674,504 A | 6/1987 | Klieman et al. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,741,337 A | 5/1988 | Smith et al. |
| 4,765,335 A | 8/1988 | Schmidt et al. |
| 4,777,949 A | 10/1988 | Perlin |
| 4,777,950 A | 10/1988 | Kees |
| 4,788,966 A | 12/1988 | Yoon |
| 4,791,707 A | 12/1988 | Tucker |
| 4,796,625 A | 1/1989 | Kees, Jr. |
| 4,796,627 A * | 1/1989 | Tucker ....................... 606/143 |
| 4,799,481 A | 1/1989 | Transue et al. |
| 4,821,721 A | 4/1989 | Chin et al. |
| 4,822,348 A | 4/1989 | Casey |
| 4,834,096 A | 5/1989 | Oh et al. |
| 4,844,066 A | 7/1989 | Stein |
| 4,854,317 A | 8/1989 | Braun |
| 4,858,608 A | 8/1989 | McQuilkin |
| 4,869,268 A | 9/1989 | Yoon |
| 4,919,152 A | 4/1990 | Ger |
| 4,934,364 A | 6/1990 | Green |
| 4,943,298 A | 7/1990 | Fujita et al. |
| 4,944,443 A | 7/1990 | Oddsen et al. |
| 4,950,258 A | 8/1990 | Kawai et al. |
| 4,961,743 A | 10/1990 | Kees et al. |
| 4,966,603 A | 10/1990 | Focelle et al. |
| 4,967,949 A | 11/1990 | Sandhaus |
| 4,976,722 A | 12/1990 | Failla |
| 4,979,950 A | 12/1990 | Transue et al. |
| 4,983,176 A | 1/1991 | Cushman et al. |
| 5,002,563 A | 3/1991 | Pyka et al. |
| 5,026,379 A | 6/1991 | Yoon |
| 5,030,226 A | 7/1991 | Green et al. |
| 5,035,692 A | 7/1991 | Lyon et al. |
| 5,037,433 A | 8/1991 | Wilk et al. |
| 5,044,540 A | 9/1991 | Dulebohn |
| 5,053,045 A | 10/1991 | Schmidt et al. |
| 5,084,057 A | 1/1992 | Green et al. |
| 5,100,420 A | 3/1992 | Green et al. |
| 5,156,608 A | 10/1992 | Troidl et al. |
| 5,156,609 A | 10/1992 | Nakao et al. |
| 5,171,249 A | 12/1992 | Stefanchik et al. |
| 5,171,250 A | 12/1992 | Yoon |
| 5,190,203 A | 3/1993 | Rodak |
| 5,192,288 A | 3/1993 | Thompson et al. |
| 5,197,970 A | 3/1993 | Green et al. |
| 5,207,692 A | 5/1993 | Kraus et al. |
| 5,217,473 A | 6/1993 | Yoon |
| 5,242,456 A * | 9/1993 | Nash et al. .................. 606/142 |
| 5,257,713 A | 11/1993 | Green et al. |
| 5,290,299 A | 3/1994 | Fain et al. |
| 5,300,081 A | 4/1994 | Young et al. |

| | | |
|---|---|---|
| 5,340,360 A | 8/1994 | Stefanchik |
| 5,342,373 A | 8/1994 | Stefanchik et al. |
| 5,364,002 A | 11/1994 | Green et al. |
| 5,366,134 A | 11/1994 | Green et al. |
| 5,368,600 A | 11/1994 | Failla et al. |
| 5,383,880 A | 1/1995 | Hooven |
| 5,389,098 A | 2/1995 | Tsuruta et al. |
| 5,395,381 A | 3/1995 | Green et al. |
| 5,431,668 A | 7/1995 | Burbank, III et al. |
| 5,431,669 A | 7/1995 | Thompson et al. |
| 5,439,468 A | 8/1995 | Schulze et al. |
| 5,474,567 A | 12/1995 | Stefanchik et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,527,318 A | 6/1996 | McGarry |
| 5,527,319 A | 6/1996 | Green et al. |
| 5,542,949 A | 8/1996 | Yoon |
| 5,547,474 A | 8/1996 | Kloekl et al. |
| 5,593,414 A | 1/1997 | Shipp et al. |
| 5,601,573 A | 2/1997 | Fogelberg et al. |
| 5,601,574 A | 2/1997 | Stefanchik et al. |
| 5,620,452 A | 4/1997 | Yoon |
| RE35,525 E | 6/1997 | Stefanchik et al. |
| 5,653,720 A | 8/1997 | Johnson et al. |
| 5,681,330 A | 10/1997 | Hughett et al. |
| 5,695,502 A | 12/1997 | Pier et al. |
| 5,700,270 A | 12/1997 | Peyser et al. |
| 5,700,271 A | 12/1997 | Whitfield et al. |
| 5,702,408 A | 12/1997 | Wales et al. |
| 5,833,700 A * | 11/1998 | Fogelberg et al. ........... 606/158 |
| 5,843,097 A | 12/1998 | Mayenberger et al. |
| 5,849,019 A | 12/1998 | Yoon |
| 5,855,590 A | 1/1999 | Malecki et al. |
| 5,858,018 A | 1/1999 | Shipp et al. |
| 5,897,565 A | 4/1999 | Foster |
| 5,921,997 A | 7/1999 | Fogelberg et al. |
| 5,993,465 A | 11/1999 | Shipp et al. |
| 6,139,555 A | 10/2000 | Hart et al. |
| 6,159,223 A | 12/2000 | Danks et al. |
| 6,193,732 B1 * | 2/2001 | Frantzen et al. ............. 606/151 |
| 6,226,843 B1 | 5/2001 | Crainich |
| 6,290,575 B1 | 9/2001 | Shipp |
| 6,350,269 B1 * | 2/2002 | Shipp et al. ................. 606/143 |
| 6,464,710 B1 * | 10/2002 | Foster ........................ 606/158 |
| 6,652,539 B2 * | 11/2003 | Shipp et al. ................. 606/143 |
| 6,652,545 B2 * | 11/2003 | Shipp et al. ................. 606/157 |

FOREIGN PATENT DOCUMENTS

| | | |
|---|---|---|
| DE | 37 22 311 | 1/1989 |
| DE | 38 02 651 | 8/1989 |
| DE | 40 15 562 | 11/1991 |
| JP | 6 237 939 | 8/1994 |
| SU | 1389 762 | 4/1988 |
| WO | WO 90 03763 | 4/1990 |

OTHER PUBLICATIONS

Nelson, Timothy M., M.D., Nakashima, Masanobu, M.D., Mulvlhill, Sean J., M.D.: "How Secure Are Laproscopically Placed Clips? An In Vitro and In Vivo Study": *Arch Surg.* 1992: 127:718-720: pub. Dec. 8, 1991.

Arnaud, Jean-Pierre, M.D., Bergamaschi, Roberto, M.D.,: "Migration and Slipping of Metal Clips After Celloscopic Cholecystomy": *Surgical Laproscopy & Endoscopy* 1993: 3(6): 487-488: pub. 1993 Raven Press, Ltd., New York.

Klein, R.D., Jessup, G., Ahari, F., Connolly, R.J., Schwaitzberg, S.D.: "Comparison of titanium and absorbable polymeric surgical clips for use in laproscopic cholecystomy": *Surgical Endoscopy* 1994: pub. 1994 Springer-Verlag New York Inc..

* cited by examiner

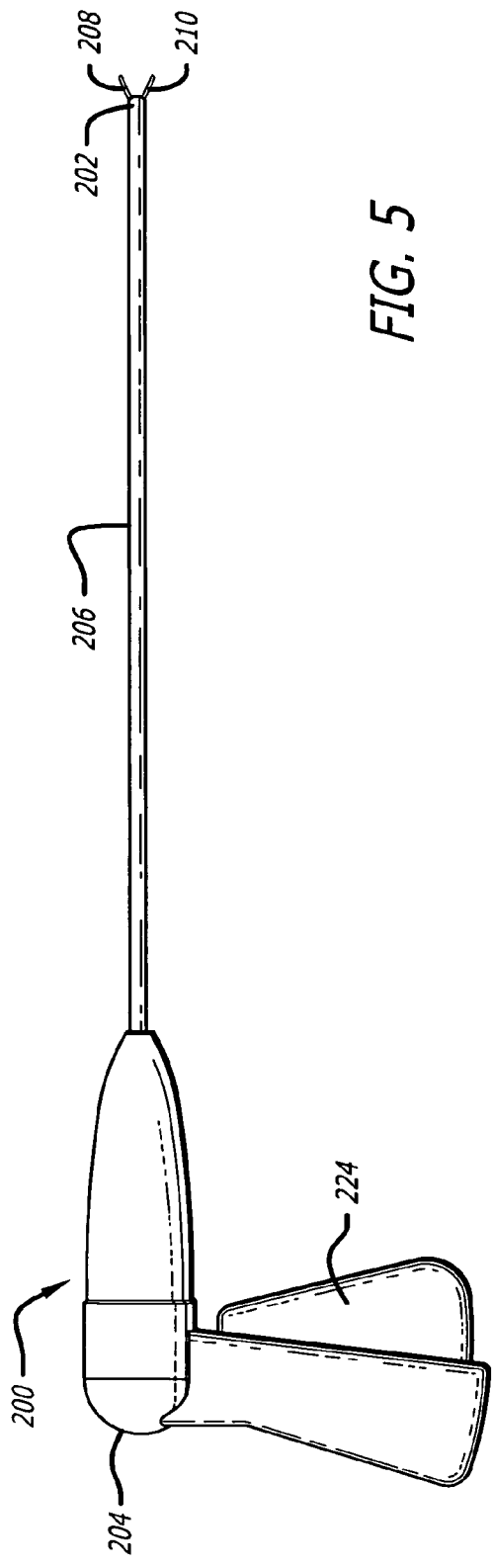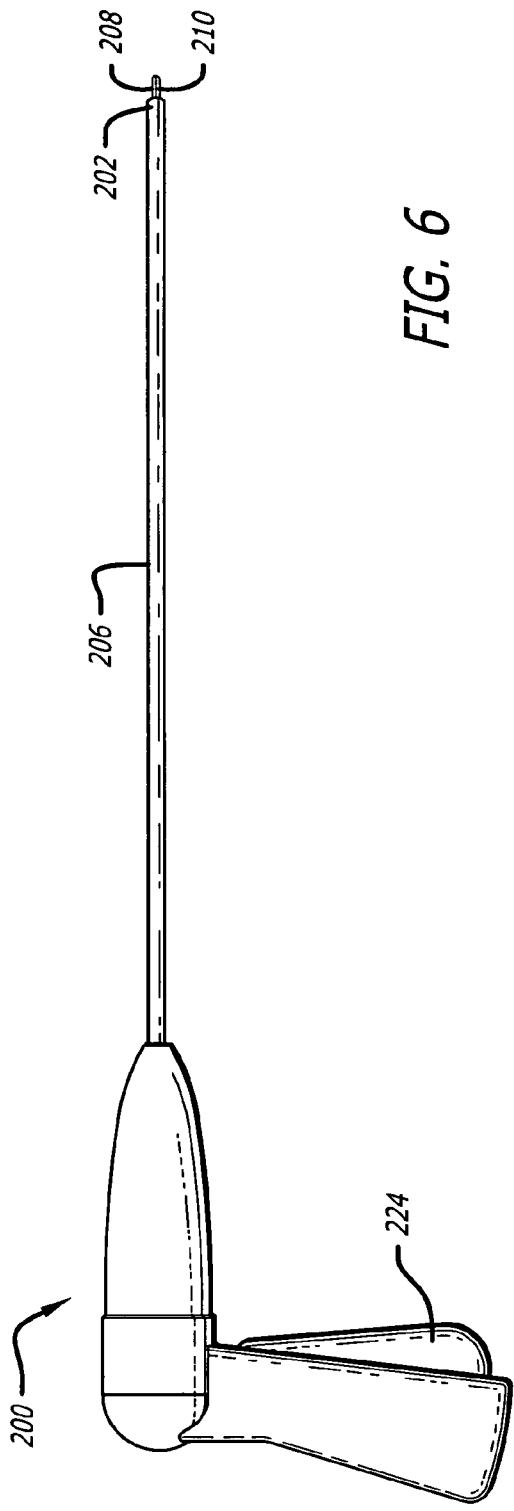

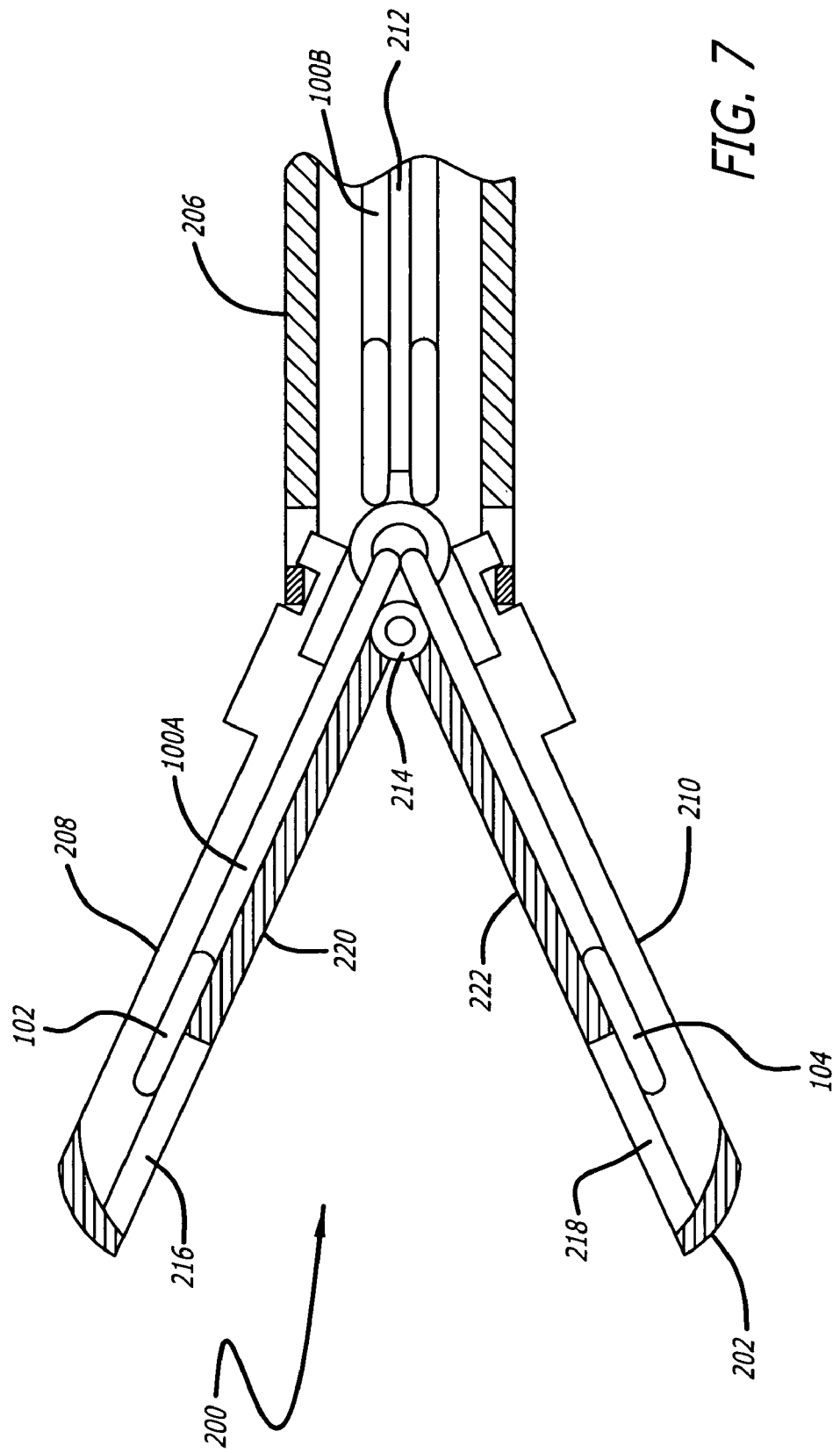

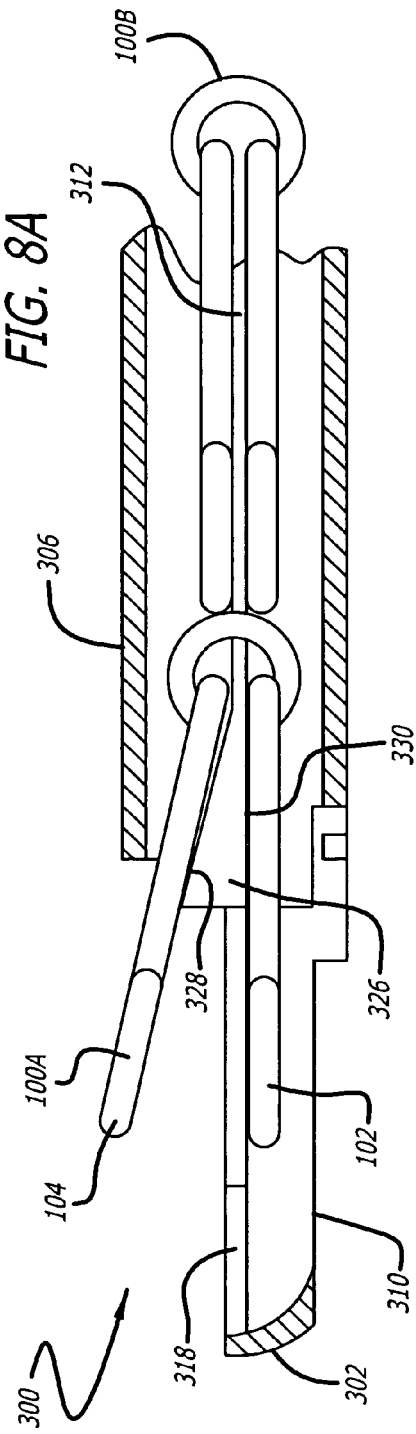

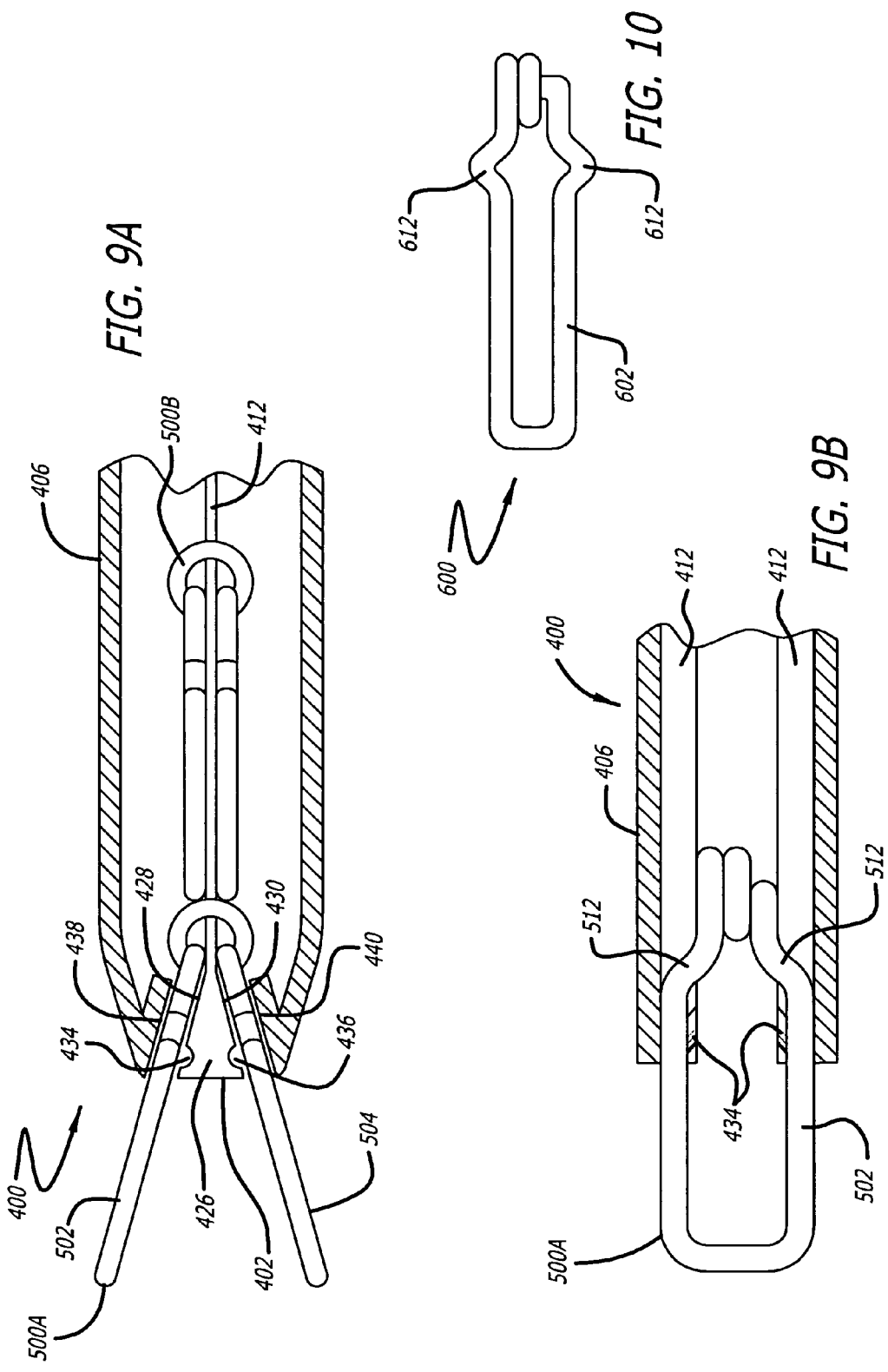

CLIP APPLIER TOOL HAVING A DISCHARGE CONFIGURATION

The present application claims the benefit of U.S. Provisional Application No. 60/513,518, filed Oct. 21, 2003, the disclosure of which is incorporated herein by reference.

BACKGROUND OF THE INVENTION

1. Field of the Invention

The present invention relates generally to mechanical devices used in surgical procedures to obtain ligation or hemostasis, and more particularly, to low profile tools that can apply a pre-formed, spring loaded ligation clip used during surgery to clamp around a vessel or duct, such as the cystic duct, and thereby obtain ligation.

2. Description of the Prior Art

It will be appreciated by those skilled in the art that the use of ligation clips to control bleeding during surgical procedures is well known. As described, for example, in U.S. Pat. Nos. 4,976,722 and 4,979,950, prior art clips are generally formed of metal wire, usually a titanium alloy, having a "U-shaped" rectangular cross-section. Such prior art clips often include a grooved pattern machined into the inner or clamping surfaces of the clip, in an attempt to enhance the ability of the clip to remain in position after it is closed around the vessel. Application of the clip to the vessel is normally effected by means of a crushing action produced by a clip applier, such as disclosed in U.S. Pat. No. 5,030,226. Such crushing actions, of course, permanently deform the clips, making them difficult to remove or re-position.

Prior art surgical ligation clips have several inherent problems. For example, the force applied by the clip to the vessel can be variable and inconsistent from one clip to the next, because of the variation in crushing force applied to the clip by the user. Further, prior art clips have a tendency to slip off the end of the blood vessel stub (i.e., perpendicular to the axis of the vessel) to which it has been applied, because of the low coefficient of friction associated with the clip, and lack of adequate restraining force provided by the clip. Because of this, separation of the clip from the vessel to which it has been applied, after the wound has been closed, is not uncommon. A related problem found in the prior art is the fact that the ligating or restraining force offered by the crushed clip varies along the length of the clip, decreasing toward the open end. Thus, the section of the vessel near the open end of the clip can be inadequately ligated.

It is also common in the prior art to actually form and crush the clip only at the time of its application to the targeted blood vessel. It is often required that the vessels of 4 mm and larger diameter be ligated. Because most clips of the prior art have no spring action it is required that the inside clearance dimension of the clip, prior to crushing, be larger than the vessel. This does not lend itself to clip applier designs that will pass through small 5 mm trocars. The applier must be inserted through a trocar, placed through the patient's external tissues, and into the surgical field. Thus, prior art ligation clip appliers used in laparoscopic procedures typically consist of a 10 mm diameter clip applier that can fit only through a trocar having a 10 to 11 mm diameter entry port. Because one goal of laparoscopic surgery is to minimize the size of the entry wound, a surgical ligation clip and clip applier that can be used within a 5 mm or even a 2.5 mm diameter trocar port is highly desirable.

New minimally invasive surgical procedures and the need for less invasiveness for current procedures require the development of smaller and smaller devices. The harvesting of saphenous veins and certain cardiovascular procedures would benefit from reduced diameters trocars, below 3 mm diameter.

To address these problems a spring action surgical clip was designed, and is disclosed in U.S. Pat. No. 5,593,414, titled "Method of Applying a Surgical Ligation Clip," the disclosure of which is incorporated herein by reference. One embodiment of the clip disclosed in the '414 patent is shown in FIGS. 1 and 2. Clip 50 has a vessel clamping arm 52, a vessel support member 54, and at least one tension coil 56 integrally joining the arm and support member. Clip 50 is pre-formed so that in its equilibrium state, it can be easily placed within the surgical field, including through an endoscopic trocar port with a diameter as little as 5 mm. After the clip is placed proximate the blood vessel or duct to be clamped, clamping arm 52 is moved from its equilibrium position to a position under higher tension, allowing positioning of the vessel between arm 52 and support member 54. When correct placement and positioning is achieved, arm 52 is released and, as the arm tends to move back towards its equilibrium position, it clamps the vessel between the arm's curved lower surface and the supporting upper surface of vessel support member 54.

To enhance the performance of the tension coil(s), vessel support member 54 includes first and second arms 58, 60, one of which terminates in a 180-degree bend section. Minimal cross-sectional area of the clip is achieved by substantially longitudinally aligning the vessel support member, the clamping arm, the 180-degree bend section 62, and the tension coil.

The clamping arm is pre-formed into an equilibrium that generally aligns with the horizontal plane of the support member. A second embodiment of the clip pre-loads the clamping arm into a pre-loaded equilibrium position where the free end of the arm rests against the upper surface of the support member.

There exists a relationship between the diameter of the trocar (hence the applier tube) and the maximum diameter of a vessel that can be ligated. Older crush clip technology limits the ratio of wound size to maximum diameter to be ligated to greater than 2. That is, to ligate a 5 mm vessel, a puncture wound of 10-12 mm is required. U.S. Pat. No. 5,593,414 teaches the method of using a spring clip that is inserted into the surgical field in the closed state, opened over a vessel, the diameter of which has been reduced, or pre-clamped, by the tool, and closed over the pre-clamped vessel. This method allows an entry wound to vessel diameter ratio of 1 or smaller. Thus, a 5 mm vessel can be ligated through a 5 mm trocar. This is substantially less invasive as compared to the older crush clip technology. For a trocar diameter of 2.5 mm, the clip can be scaled down to approximately half size on the wire diameter, coil height, and length, yet still supply an acceptable ligation force on a 2.5 mm vessel.

Unfortunately, several problems are encountered in applying the spring-action ligation clip of U.S. Pat. No. 5,593,414 to a vessel through a 5 mm or smaller trocar port. First, the nominal 5 mm cross-section of the clip that is inserted through the trocar places severe design restrictions on any applier mechanism. Second, care must be taken so that the elastic limit of the spring material is not exceeded when the clip is opened up so that it can be placed over the vessel diameter. For a titanium wire of diameter 0.75 mm, for example, lifting a distal end of a spring clip much above a few mm will exceed the elastic limit. Secondly, these spring clips are small and compact and owing to the preload, have a great deal of energy stored in the spring. As these clips are opened to place them over a vessel the stored energy increases substantially, in some cases more than doubling. This energy makes controlling the clip, to insure proper installation, difficult. Undesirable translation or rotation can result in misplacement or dropping of the clip inside the body.

Another approach which has been proposed to provide smaller diameter endoscopic clip application is that of U.S. Pat. No. 5,601,573 to Fogelberg et al. Fogelberg et al. still struggles with the complex manipulation required to advance the clip in a closed position and then open the clip prior to placement. Fogelberg et al. also has an overly complex multistage trigger arrangement for actuation of the jaws and the clip advancement mechanism. The present invention presents several improvements over Fogelberg et al. including the advancement of the clips in an open or semi-open position rather than a closed position.

The clip and clip applier disclosed in U.S. Pat. No. 6,350,269, titled "Ligation Clip and Clip Applier" and filed Mar. 1, 1999, the disclosure of which is incorporated herein by reference, represents a further improvement over the Fogelberg et al. device. The '269 patent discloses a clip having wire loops at one end thereof and a clip applier that utilizes the loop width to open and release the clip around a vessel.

There are several problems associated with the spring clip applicators of the prior art. For example, one problem is that the diverging surfaces of the jaws often obstruct the surgeon's view of the tissue to be ligated owing to the acute angle of the laparoscopic camera and the clip applier.

What is needed then is a clip applier without jaws, or with a single, fixed jaw so that the surgeon has a better view of the tissue to be ligated. Such a configuration also eliminates the severe pinching force on tissue that might be located near the axis or pivot point of an applicator having two jaws rotatable relative to one another. Additionally, the need to pre-clamp the tissue or vessel can be eliminated when a guide surface is provided that opens the clip to a sufficient height to be inserted over the vessel or tissue. The omission of the pre-clamping step eliminates any possible structural damage to the vessel or tissue that may otherwise be caused if the surgeon were to change his or her mind after clamping the vessel or tissue before applying the clip.

In the alternative, what is needed is a clip applier having jaws that remain in an open position until a clip is nearly at a release point along the jaws. Such a configuration allows the surgeon a last opportunity to carefully visualize the vessel to be ligated before clamping and attaching the ligation clip to the vessel.

SUMMARY OF THE INVENTION

In one preferred embodiment of the present invention, a method of ligating a fluid carrying structure includes inserting into a patient a surgical ligation instrument having upper and lower clamping surfaces moveable relative to one another between an open position for receiving the fluid carrying structure and a closed position for compressing the fluid carrying structure therebetween. The upper and lower clamping surfaces are adapted to contact the fluid carrying structure. The method further includes positioning the fluid carrying structure between the clamping surfaces of the instrument; moving a ligation clip over a portion of the clamping surfaces of the instrument overlying a portion of the fluid carrying structure while the clamping surfaces are in the open position, the ligation clip being resiliently biased to a closed position; moving the upper and lower clamping surfaces to the closed position while the ligation clip is over the clamping surfaces; and releasing the ligation clip to permit the ligation clip to move to the closed position of the ligation clip.

In another preferred embodiment of the present invention, an apparatus for compressing a fluid carrying structure includes a proximal end, an opposite distal end for insertion first into a patient, and a mid-longitudinal axis passing through the proximal and distal ends. The distal end does not have any portion adapted to move away from the mid-longitudinal axis. The shaft has a passage adapted to receive at least one surgical ligation clip therein, the clip being biased to a closed position. The shaft has a guide surface adapted to move the clip to an open position.

In yet another preferred embodiment of the present invention, a surgical ligation apparatus for compressing a fluid carrying structure includes a proximal end, an opposite distal end adapted to be inserted first into a patient, and a mid-longitudinal axis passing through the proximal and distal ends. The apparatus further includes a shaft having a passage adapted to receive at least one surgical ligation clip therein, the ligation clip having a length and being biased to a closed position. The shaft has a guide surface proximate the distal end adapted to move the ligation clip to an open position. The guide surface is adapted to retain the ligation clip in the open position while a majority of the length of the ligation clip is beyond the distal end of the apparatus.

Another preferred method of the present invention includes inserting a ligation clip that is biased to a closed position into a trocar having a maximum transverse cross sectional dimension; opening the ligation clip to a height greater than the maximum transverse cross sectional dimension of the trocar; and ligating a vessel or tissue without pre-clamping the vessel or tissue. The ligation clip may be opened to a height between 3 mm to 10 mm for a 3 mm or 5 mm diameter trocar.

These and other objects of the present invention will be apparent from review of the following specification and the accompanying drawings.

BRIEF DESCRIPTION OF THE DRAWINGS

FIG. 5 is a side elevation view of a clip applier having a distal end with a pair of compression members in an open position in accordance with one embodiment of the present invention.

FIG. 6 is a side elevation view of the clip applier of FIG. 5 with the compression members in a closed position.

FIG. 7 is an enlarged fragmentary cross sectional side view of the distal end of the clip applier of FIG. 5.

FIG. 8A is an enlarged fragmentary cross sectional side view of the distal end of a clip applier in accordance with another preferred embodiment of the present invention.

FIG. 8B is an enlarged fragmentary cross sectional top view of the distal end of the clip applier of FIG. 8A.

FIG. 9A is an enlarged fragmentary cross sectional side view of the distal end of a clip applier in accordance with another preferred embodiment of the present invention.

FIG. 9B is an enlarged fragmentary cross sectional top view of the distal end of the clip applier of FIG. 9A.

FIG. 10 is a top plan view of another embodiment of a ligation clip for use with the clip applier of FIG. 9A.

DETAILED DESCRIPTION OF THE PREFERRED EMBODIMENT

Reference will now be made in detail to the present preferred embodiments (exemplary embodiments) of the invention, examples of which are illustrated in the accompanying drawings.

Figure 1:
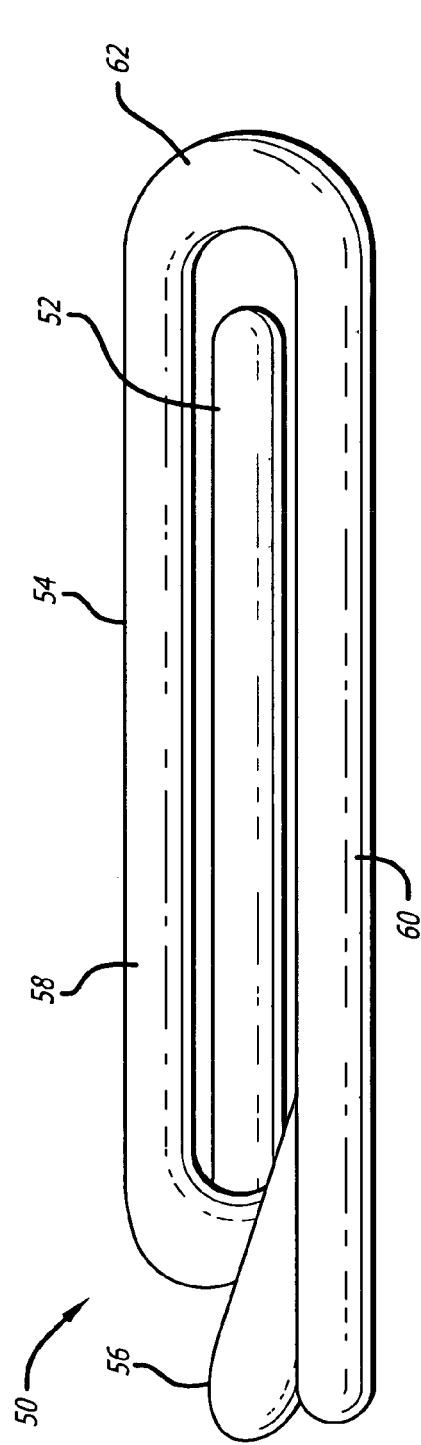
FIG. 1 is a top plan view of a surgical ligation clip disclosed in the prior art.
Figure 2:
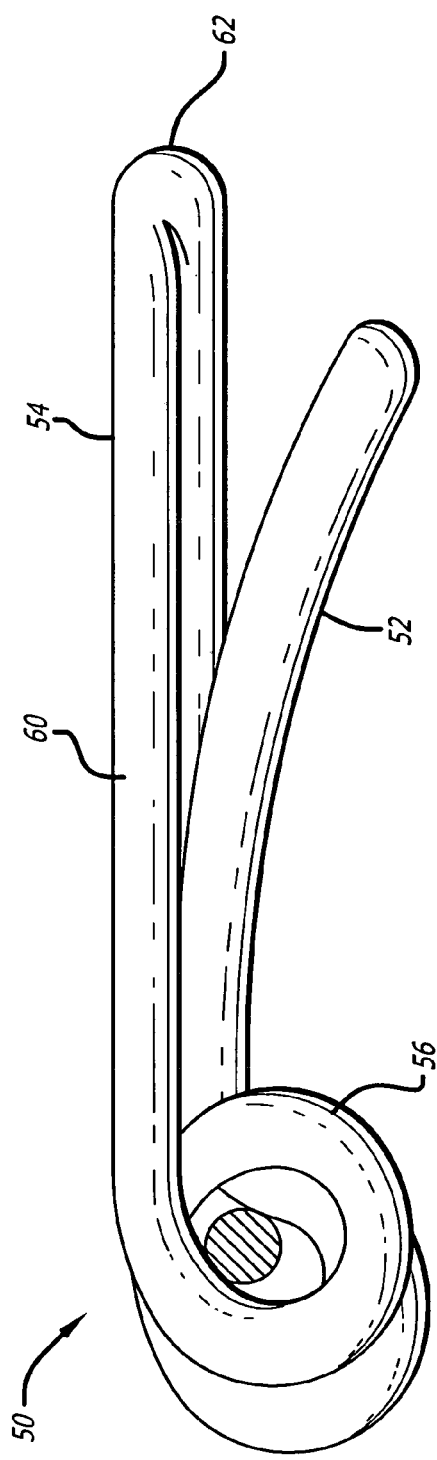
FIG. 2 is a side elevation view of the surgical ligation clip of FIG. 1.
Figure 3:
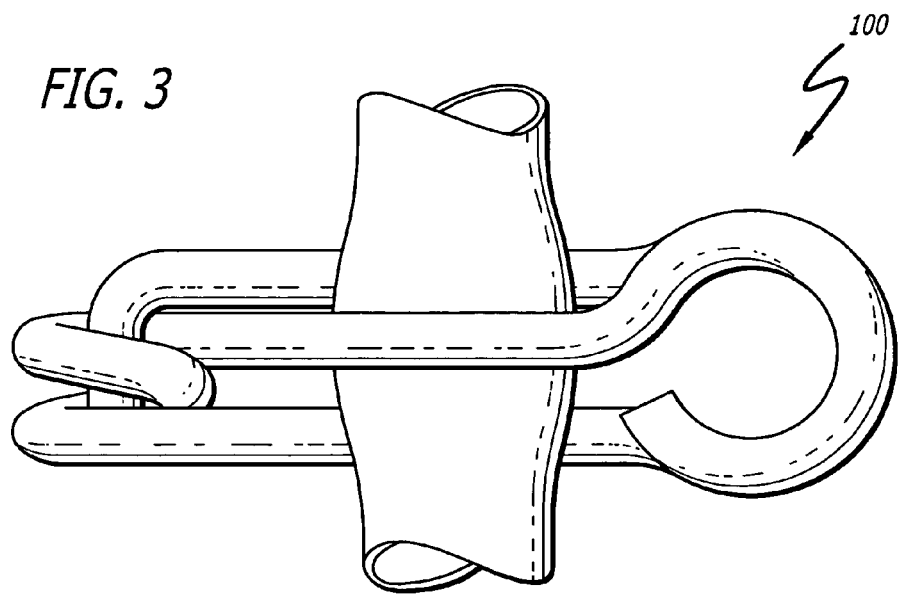
FIG. 3 is a top plan view of a surgical ligation clip in accordance with another embodiment of the present invention, the surgical ligation clip being engaged about a vessel.
Figure 4:
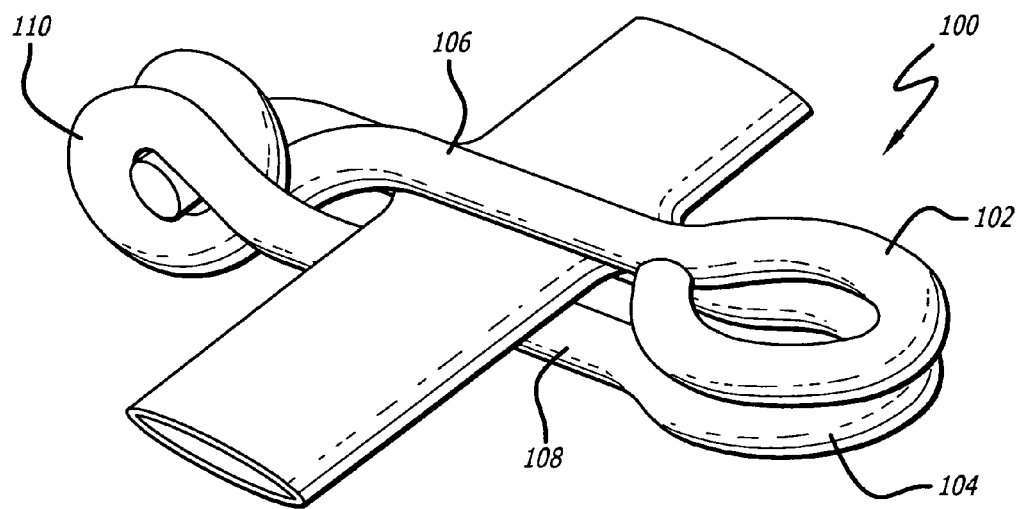
FIG. 4 is a perspective view of the surgical ligation clip of FIG. 3.

FIGS. 3 and 4 show an example of a surgical ligation clip 100 usable with a preferred embodiment of the clip applier of the present invention. Surgical ligation clip 100 includes a clamping arm 106 and a support member 108. A coil tension spring 110, which may also be generally referred to as a connector, joins clamping arm 106 and support member 108.

Clamping arm 106 has a first enlarged end 102 defined thereon. Support member 108 has a second enlarged end 104 defined thereon. The first and second enlarged ends 102, 104 are first and second wire loops which are integrally formed with clamping arm 106 and support member 108 of clip 100.

Loops 102, 104, and particularly the laterally outer portions thereof, may be described as first and second control surfaces being received in and trapped within the first and second channels of a shaft or clip carrier. As best seen in FIG. 8A, a plurality of ligating clips 100 are received in shaft 206 in a semi-open position. For ease of identification, consecutive clips beginning with the forward-most one are designated as 100A, 100B, 100C, etc. The control surfaces, as engaged by the channels in the passage of the shaft, prevent rotation and yawing of clip 100 as the clip is moved through the shaft.

The connector of clamping arm 106 and support member 108 is preferably a coil spring 110 which has a preload that biases the support member 108 and clamping arm 106 toward each other. The preload is preferably such that when clip 100 is oriented toward the closed or pre-loaded equilibrium position shown in FIGS. 3 and 4, there is still a spring preload in the connector which forces wire loops 102, 104 against each other.

As shown in FIGS. 3 and 4, clip 100 has a length which is adapted to span a majority of the width of a fluid carrying structure. As defined herein, the "width" of the fluid carrying structure is the cross sectional distance from one side of the fluid carrying structure to the other side of the fluid carrying structure.

FIGS. 5 and 6 show one preferred embodiment of a clip applier 200 in accordance with the present invention. Clip applier 200 includes a distal end 202, a proximal end 204, and a tubular shaft 206 therebetween. Distal end 202 includes upper and lower compression members 208, 210 that are moveable between an open position, shown in FIG. 5, and a closed position, shown in FIG. 6.

FIG. 7 shows a ligation clip 100A being advanced along a pair of opposed rails 212 projecting from the interior sides of shaft 206. Only one of the opposed side rails 212 is shown in FIG. 7. Rails 212 extend along the length of shaft 206 and are configured to maintain clips 100 in a slightly open position as they are moved along the length of shaft 206 and into engagement with compression members 208, 210. Rails 212 preferably have a thickness of approximately 0.005 inches. The clips may be pushed against one another, or moved along shaft 206 by a pusher rod having a plurality of prongs extending therefrom for individually engaging clips contained in a clip carrier, such as taught in the '269 patent. It will be understood that other methods for advancing the clips forward may be used without departing from the scope of the present invention.

Upper and lower compression members 208, 210 are preferably hingedly connected to shaft 206. A coil spring 214 around the hinge biases upper and lower compression members 208, 210 apart to an open position, such as shown in FIG. 7. Each side of clip applier 200 preferably includes a hinge and coil spring.

It will be appreciated that although two springs are described to bias the compression members open, a single spring or other mechanical equivalents may be used to bias the compression members. For example, a leaf spring may be used to bias the compression members.

Alternatively, instead of biasing the compression members apart, the proximal ends of the compression members may be cammed for use with a two-stage trigger so that a first squeeze will pre-clamp the tissue or vessel when the clip is near the release openings, for example, 2 mm away, and a continued second squeeze of trigger 224 will discharge a clip 100A. A two-stage trigger permits the surgeon the opportunity to evaluate whether the vessel or tissue is sufficiently pre-clamped before discharging a clip. An example of a trigger adaptable for use with the present invention is taught in the '269 patent.

With reference to FIG. 7, the operation of clip applier 200 will now be described. The forward-most clip 100A is pushed out of shaft 206 into upper and lower compression members 208, 210 by the next adjacent clip 100B. As forward-most clip 100A is pushed forward, the lateral sides of wire loops 102, 104 slide along rails 212 of the clip carrier in a semi-open position owing to the biasing force towards the closed position of clip 100A against each rail. Continued forward movement of clip 100A along the length of the clip applier brings the lateral sides of wire loops 102, 104 into contact with rails located within each compression member. As clip 100A is pushed into compression members 208, 210, spring 214 exerts a biasing force on compression members 208, 210 to bias compression members 208, 210 open until clip 100A has traveled to within 2 mm of drop-off or release openings 216, 218 on compression members 208, 210, respectively. At this point, the biasing force exerted by coil 110 of clip 100A to close clip 100A overcomes the biasing force of spring 214 and causes compression members 208, 210 to close about a vessel or tissue about to be ligated. Continued advancement of clip 100A towards release openings 216, 218 brings wire loops 102, 104 into registry with release openings 216, 218. Support member 106 and clamping arm 108 of clip 100A then snap shut toward each other, thus clamping a vessel or tissue therebetween as clip 100A is released from upper and lower compression members 208, 210.

The closing motion of compression members 208, 210 may be described as pre-clamping the vessel or tissue by movement of upper and lower clamping surfaces 220, 222 toward one another. It is noted that the step of pre-clamping the vessel or tissue between upper and lower compression members 208, 210 typically occurs prior to the step of pushing clip 100A completely from upper and lower compression members 208, 210.

It is further noted that the method of operating clip applier 200 may include the steps of loading in a plurality of clips 100 into the shaft or a clip carrier such that wire loops 102, 104 are received within channels with the clips thus held in a semi-open position by rails 212. Then, each time that trigger 224 is compressed, each clip 100 is advanced forward in the shaft or clip carrier. Clips 100 are preferably arranged in the shaft or clip carrier in a head to tail orientation. During this procedure, rotation of clip 100 is prevented by containing wire loops 102, 104 in the passage of the shaft or clip carrier.

Upper and lower compression members 208, 210 are preferably in a closed position to insert clip applier 200 into the trocar. The proximal ends of upper and lower compression members 208, 210 may be pulled toward the proximal end of the clip applier to close the compression members, or a portion of the clip applier may be advanced forward to ride over a portion of the compression members to move the compression members to the closed position for insertion into the trocar. For example, clip applier 200 may be adapted for use with a clip carrier such as taught in the '269 patent. As taught in the '269 patent, a portion of the shaft is moveable relative to the clip carrier to close the compression members and insert the clip applier through the trocar.

Another embodiment of the clip applier of the present invention is shown in FIGS. 8A and 8B and is generally referred to by the reference number 300. Clip applier 300 is generally similar to clip applier 200 except that clip applier 300 has only one compression member 310. Clip applier 300 also includes a pair of opposed guide surfaces 326 along the interior of shaft 306. Guide surfaces 326 are preferably wedge-shaped and include upper and lower portions 328, 330, respectively. Upper and lower portions 328, 330 act to force apart wire loops 102, 104 of clip 100 as the clip is advanced toward distal end 302 of clip applier 300. As shown in FIG. 8A, upper portion 328 of guide surface 326 is inclined away from the mid-longitudinal axis of the clip applier, while lower portion 330 is generally parallel with the mid-longitudinal axis of the clip applier.

Guide surfaces 326 also preferably include a portion 332 that slopes inward toward the mid-longitudinal axis of the clip applier and toward distal end 302. Opposed portions 332 act to center coil 110 of clip 100 as clip 100 is advanced towards a released position in which clip 100 is released from clip applier 300.

Preferably, guide surfaces 326 are integrally formed with shaft 306 and are therefore fixed along the length of shaft 306. In this configuration, no movement of the clip applier is necessary to open clips 100 to the open position other than that needed to push the clips along shaft 306. This eliminates the separate pre-clamping step found in some conventional clip appliers.

Guide surfaces 326 may also be laterally flexible so that as a clip rides over each guide surface, a predetermined amount of pressure caused by the force biasing the clip closed will cause the guide surfaces to flex laterally away from the mid-longitudinal axis and allow the clip to move to the closed position. The sides of the shaft may be slotted in order to accommodate the flexible movement of the guide surfaces. The displacement of flexible guide surfaces may also be accomplished by mechanical actuation such as with the use of a rod connected to the handle that cams against one or both of the guide surfaces to move the guide surfaces.

With reference to FIGS. 8A and 8B, the operation of clip applier 300 will now be described. FIG. 8A shows clip applier 300 with clip 100A approaching the pre-release position. After a surgeon has inserted clip applier 300 through a trocar and into a patient, the surgeon squeezes the trigger of clip applier 300 to advance clip 100A along rails 312 and toward guide surfaces 326. As the lateral sides of the upper and lower wire loops of clip 100A ride over upper and lower portions 328, 330 of guide surfaces 326, clip 100A is opened. Continued advancement of clip 100A moves wire loop 104 out of the clip applier while one of the arms of support member 108 (FIGS. 3 and 4) continues riding up one of guide surfaces 326 until clip 100A is in a pre-release position as shown in FIG. 8A.

Once the clip is in the pre-release position, the surgeon positions a fluid carrying structure such as a vessel or stub end of a tissue between the upper and lower loop sections of the clip. Further squeezing the trigger on the handle of clip applier 300 will cause the clip to move out of the pre-release position and off the guide surfaces of the clip applier until release opening 318 in fixed compression member 310 allows the release of wire loop 102 of clip 100A, simultaneously releasing clip 100A from guide surfaces 326. As the clip leaves the clip applier, the clip is no longer restrained in the open position, allowing the clip to move to the closed position. A subsequent clip 100B may then be readied for deployment in the manner described above.

It will be appreciated that the distance between guide surfaces 326 and release opening 318 may be varied so that the clip is allowed to move to the closed position before wire loop 102 comes into registry with release opening 318. The vessel or tissue may then be ligated by the clip prior to the release of the clip from the clip applier. The clip may then be released from the clip applier by pushing the clip toward the distal end of the clip applier.

Another embodiment of the clip applier of the present invention is shown in FIGS. 9A and 9B and is generally referred to by the reference number 400. Clip applier 400 is generally similar to clip applier 300 except that clip applier 400 does not have any compression members at the distal end of the clip applier. Instead, upper and lower portions 428, 430 of guide surfaces 426 each include upper and lower indented portions 434, 436, respectively. Upper and lower indented portions 434, 436 are sized to receive a portion of a clip 500.

Clip 500 has upper and lower wire loop sections 502, 504 with a transverse width sufficient enough to contact both of opposed rails 412. Clip 500 also includes arm sections 512 that are generally non-parallel to the mid-longitudinal axis of clip 500. Arm sections 512 of upper loop 502 are configured to be received in upper indented portions 434 of guide surfaces 426. As clip 500 is moved along guide surfaces 426, arm sections 512 of upper and lower loop sections 502, 504 will encounter upper and lower indented portions 434, 436 and be seated therein owing to the force biasing clip 500 toward the closed position. This allows the clip to be offered up to the tissue or vessel before the clip is finally positioned. Continued advancement of clip 500 will move arm sections 512 out of upper and lower indented portions 434, 436 and off guide surfaces 426.

It will be appreciated that other clip configurations are useable with the clip applier of the present invention. For example, a less invasive clip 600 is shown in FIG. 10. Ligation clip 600 is similar to ligation clip 500 except that ligation clip 600 has a reduced transverse width along a majority of the length of the clip. Ligation clip 600 includes arm sections 612 that represent the widest part of the clip. Arm sections 612 are positioned near the proximal end of the clip so that most of the clip will be in an open and ready position when arm sections 612 rest in indented portions 428 of guide surfaces 420. Clips 500 and 600 may be adapted for use with clip applier 300 by forming the upper member with a width near the proximal end of the clip that is sufficient to contact one or both of guide surfaces 426 while forming the lower member with a loop at the distal end of the clip.

Upper and lower indented portions 434, 436 of guide surfaces 426 may be oriented so as to adjust the degree of effort needed to move the clip from a pre-release position, where the arms of the clip rest in the indented portions, to a final deployed position where the clip is disengaged from the clip applier. As shown in FIG. 9B, upper indented portions 434 may form a channel that are angled relative to the mid-longitudinal axis of the clip applier to receive similarly oriented arm sections 512 of ligation clip 500. The angle of the channel will affect to some extent the amount of force needed to overcome the biasing force of the clip. In particular, the more angled the channel, the less resistance will be encountered to move the clip out of upper and lower indented portions 434, 436.

Upper and lower indented portions 434, 436 may form channels oriented generally perpendicular to the mid-longitudinal axis of the clip applier. This will provide a greater resistance in the pre-release position and assist in guarding against accidental release of the clip prior to the final positioning of the clip over the vessel or tissue to be ligated. It will be appreciated that the clip may be held in the pre-release position by restricting other portions of the clip. Indented portions 434, 436 may be omitted if a quick-action, single-actuation clip application is desired.

As shown in FIG. 9A, the upper and lower portions of shaft 406 may include upper and lower guide surfaces 438, 440 oriented toward the mid-longitudinal axis of the clip applier and generally facing toward guide surfaces 426. Upper and lower guide surfaces 438, 440 act with guide surfaces 426 to create guide channels for the lateral portions of upper and lower wire loops 502, 504. Guide surfaces 438, 440 are spaced an appropriate distance from guide surfaces 426 in order to accommodate the travel of the ligation clip therebetween.

With reference to FIGS. 9A and 9B, the operation of clip applier 400 will now be described. FIG. 9A shows clip applier 400 with ligation clip 500A approaching the pre-release position. After a surgeon has inserted clip applier 400 through a trocar and into the patient, the surgeon squeezes the trigger of clip applier 400 to advance ligation clip 500A toward the pre-release position as shown in FIG. 9A. Once the clip is in the pre-release position with the arm sections of the clip resting in upper and lower indented portions 434, 436 of guide surfaces 426, the surgeon positions the fluid carrying structure between upper and lower wire loop sections 502, 504 of clip 500A. Further squeezing the trigger on the handle of clip applier 400 will cause clip 500A to move out of the pre-release position and off the guide surfaces of the clip applier. As clip 500A leaves the clip applier, upper and lower loop sections 502, 504 are no longer restrained in the open position, allowing clip 500A to move to the closed position. A subsequent ligation clip 500B may then be readied for deployment in the manner described above.

The embodiment shown in FIGS. 9A and 9B has the advantage of being easily positioned once inserted through the trocar. Further, using guide surfaces that can be adapted to open the clip to a height greater than the maximum transverse cross sectional dimension of the trocar reduces or eliminates the need for any pre-clamping step, making the over-all surgical procedure more efficient.

For the embodiments shown in FIGS. 8A to 9B, it will be appreciated that although two opposed guide surfaces are shown, one on each side of the interior of the shaft, a single guide surface may be adapted to open the clip according to the configuration of the clip.

For any of the embodiments described above, the clip applier may be made of a material suitable for use in surgery, for example, a surgical grade metal or plastic. Certain components of the clip applier may be made disposable or replaceable. For example, referring to FIGS. 5, 8A, and 9A, the shaft may be detachable from the handle. The handle can then be used with a set of shafts having different shaft lengths or configurations. The shaft can also be made disposable. The attachment of the shaft and the handle may be by way of snap-fit or screw-threaded engagement. In embodiments where the shaft is permanently affixed to the handle, the inner passage of the shaft may be configured to receive a clip carrier such as described in the '269 patent.

The ligation clips described herein are exemplary only. Ligation clips having more than one coil, or even no coils, but otherwise exhibiting a resilient characteristic may be used with the clip applier of the present invention. For example, clips including a shape memory alloy such as nitinol may be advanced along the shaft in a semi-open position and deployed in a further opened position around the vessel or tissue to be ligated. The increase in temperature around the clip will then cause the clip to ligate the vessel or tissue.

It will be appreciated by those skilled in the art that the features described in relation to one embodiment may be combined or substituted with the features of other embodiments without departing from the scope of the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A surgical ligation apparatus for compressing a fluid carrying structure, comprising:

at least one ligation clip comprising a length with a proximal end and an opposite distal end, and opposed contact surfaces for contacting the fluid carrying structure being biased toward one another, said opposed contact surfaces moveable from at least a first position to a maximum open position; and a ligation clip applier having:

a proximal end, an opposite distal end for insertion first into a patient, and a mid-longitudinal axis passing through and a length extending between said proximal and distal ends, said distal end having no portion adapted to move away from the mid-longitudinal axis;

a shaft having a passage adapted to receive said ligation clip therein, said shaft having guide surfaces proximate said distal end, and rails including first and second sides extending along at least a portion of said length of said clip applier to said guide surfaces, said first side adapted to contact one of said opposed contact surfaces of said ligation clip and said second side adapted to contact another of said opposed contact surfaces of said ligation clip, said rails adapted to facilitate advancement of said ligation clip therealong to said guide surfaces with said opposed contact surfaces spaced apart from one another in the first position, said guide surfaces including first portions adapted to be positioned between and contact said opposed contact surfaces of said ligation clip to move said clip to the maximum open position and facilitate contact of said opposed contact surfaces with the fluid carrying structure; and at least one indentation formed in said first portions of said guide surfaces, said at least one indentation sized to receive a portion of said ligation clip, said clip prior to release thereof from said clip applier being maintained in a pre-release position with said opposed contact surfaces being spaced apart from one another when said portion thereof is received in said at least one indentation, the distance between said opposed contact surfaces of said ligation clip in the pre-release position being greater than in the first position, and being less than in the maximum open position, wherein the fluid carrying structure can be received between said opposed contact surfaces of said ligation clip when said clip is in the pre-release position with said portion of said clip received in said at least one indentation.

2. The apparatus of claim 1, wherein said distal end of said ligation clip applier has no portion adapted to move along the mid-longitudinal axis of said apparatus.

3. The apparatus of claim 1, further comprising a clip carrier moveable within said passage of said shaft for holding a plurality of surgical ligation clips therein.

4. The apparatus of claim 1, wherein said first portions of said guide surfaces of said ligation clip applier are wedge-shaped.

5. The apparatus of claim 1, wherein said first portions of said guide surfaces of said clip applier open said ligation clip immediately before said clip compresses the fluid carrying structure.

6. The apparatus of claim 1, wherein said first portions of said guide surfaces of said clip applier are adapted to transition said ligation clip from the first position to the maximum open position.

7. The apparatus of claim 1, wherein said first portions of said guide surfaces of said clip applier contact said opposed contact surfaces to wedge said ligation clip into the maximum open position.

8. The apparatus of claim 1, further comprising second portions of said guide surfaces of said clip applier adapted to contact said proximal end of said ligation clip to align said clip with the mid-longitudinal axis of said clip applier.

9. The apparatus of claim 8, wherein said second portions of said guide surfaces of said clip applier face said mid-longitudinal axis of clip applier.

10. A surgical ligation apparatus for compressing a fluid carrying structure, comprising:
   at least one surgical ligation clip having a length with a proximal end and an opposite distal end, and opposed contact surfaces for contacting the fluid carrying structure being biased toward one another and disposed between said proximal end and said distal end; and
   a ligation clip applier having:
   a proximal end, an opposite distal end adapted to be inserted first into a patient, and a mid-longitudinal axis passing through and a length extending between said proximal and distal ends, said distal end of said clip applier being fixed relative to the mid-longitudinal axis;
   a shaft having a passage adapted to receive said ligation clip therein, said shaft having guide surfaces proximate said distal end, and rails including first and second sides extending along at least a portion of said length of said clip applier to said guide surfaces, said first side adapted to contact one of said opposed contact surfaces of said ligation clip and said second side adapted to contact another of said opposed contact surfaces of said ligation clip, said rails adapted to facilitate advancement said ligation clip therealong to said guide surfaces with said opposed contact surfaces spaced apart from one another in a first position, and said guide surfaces including first portions adapted to contact said opposed contact surfaces of said ligation clip to move said clip to a maximum open position, and second portions adapted to contact said proximal ends of said ligation clip to align said clip with the mid-longitudinal axis of said apparatus, while said distal end of said ligation clip and a majority of said length thereof is beyond said distal end of said apparatus;
   at least one indentation formed in said first portions of said guide surfaces, said at least one indentation sized to receive a portion of said ligation clip, said ligation clip prior to release thereof from said clip applier being maintained in a pre-release position with said opposed contact surfaces being spaced apart from one another when said portion thereof is received in said at least one indentation, the distance between said opposed contact surfaces of said ligation clip in the pre-release position being greater than in the first position, and being less than in the maximum open position, wherein the fluid carrying structure can be received between said opposed contact surfaces of said ligation clip when said clip is in the pre-release position with said portion of said clip received in said at least one indentation; and
   a clip carrier moveable within said passage of said shaft for holding a plurality of surgical ligation clips therein.

11. The apparatus of claim 10, wherein said guide surfaces are located substantially within said shaft.

12. The apparatus of claim 10, wherein said first portions of said guide surfaces of said clip applier are wedge-shaped.

13. The apparatus of claim 10, wherein each of said first portions of said guide surfaces of said clip applier have upper and lower portions adapted to move apart two portions of said ligation clip.

14. The apparatus of claim 10, wherein said first portions of said guide surfaces of said clip applier open said ligation clip immediately before said clip compresses the fluid carrying structure.

15. The apparatus of claim 10, wherein said first portions of said guide surfaces of said clip applier are adapted to transition said ligation clip from the first position to the maximum open position.

16. The apparatus of claim 10, wherein said first portions of said guide surfaces of said clip applier contact said opposed contact surfaces to wedge said ligation clip into the maximum open position.

17. The apparatus of claim 10, wherein said second portions of said guide surfaces of said clip applier face said mid-longitudinal axis of said clip applier.

18. A surgical ligation apparatus for compressing a fluid carrying structure, comprising:
   a plurality of surgical ligation clips, each of said ligation clips comprising a length with a proximal end and an opposite distal end, and opposed contact surfaces for contacting the fluid carrying structure being biased toward one another and disposed between said proximal end and said distal end; and
   a ligation clip applier comprising:
   a proximal end, an opposite distal end for insertion first into a patient, and a mid-longitudinal axis passing through and a length extending between said proximal and distal ends, said distal end of said clip applier being fixed relative to the mid-longitudinal axis;
   a shaft having a passage adapted to receive a plurality of surgical ligation clips therein, said shaft having guide surfaces proximate said distal end, and rails including first and second sides extending along at least a portion of said length of said clip applier to said guide surfaces, said first side adapted to contact one of opposed contact surfaces of each of said ligation clips and said second side adapted to contact another of said opposed contact surfaces of each of said ligation clips, said rails adapted to facilitate advancement of said ligation clips therealong to said guide surfaces with said opposed contact surfaces spaced apart from one another in a first position, and said guide surfaces including first portions adapted to be positioned between said opposed contact surfaces to move each of said ligation clips to a maximum open position, and second portions adapted to contact said proximal ends of each of said ligation clips, said first portions contacting said opposed contact surfaces and said second portions contacting said proximal ends of said ligation clips simultaneously, immediately before said ligation clips are released from said apparatus; and at least one indentation formed in said first portions of said guide surfaces, said at least one indentation sized to receive a portion of each of said ligation clips, said ligations clips prior to release thereof from said clip applier being maintained in a pre-release position with said opposed contact surfaces being spaced apart from one another when said portion thereof is received in said at least one indentation, the distance between said opposed contact surfaces of each of said ligation clips in the pre-release position being greater than in the first position, and being less than in the maximum open position, wherein the fluid carrying structure can be received between said opposed contact surfaces of each of said ligation clips when said clips are in the pre-release position with said portion of said clips received in said at least one indentation.

19. The apparatus of claim 18, wherein said distal end of said clip applier has no portion adapted to move along the mid-longitudinal axis thereof.

20. The apparatus of claim 18, further comprising a clip carrier moveable within said passage of said shaft for holding said plurality of surgical ligation clips therein.

21. The apparatus of claim 18, wherein said first portions of guide surfaces of said clip applier are wedge-shaped.

22. The apparatus of claim 18, wherein said first portions of said guide surfaces of said clip applier open said ligation clips immediately before said clips compress the fluid carrying structure.

23. The apparatus of claim 18, wherein said first portions of said guide surfaces of said clip applier are adapted to transition each of said ligation clips from the first position to the maximum open position.

24. The apparatus of claim 18, wherein said first portions of said guide surfaces of said applier contact said opposed contact surfaces to wedge each of said ligation clips into the maximum open position.

25. The apparatus of claim 18, wherein said second portions of said guide surfaces of said clip applier are adapted to contact said proximal end of each of said ligation clips to align said clips with the mid-longitudinal axis of said clip applier.

26. The apparatus of claim 18, wherein said second portions of said guide surfaces face said mid-longitudinal axis of said clip applier.

* * * * *

UNITED STATES PATENT AND TRADEMARK OFFICE
CERTIFICATE OF CORRECTION

PATENT NO. : 7,572,266 B2 Page 1 of 1
APPLICATION NO. : 10/969138
DATED : August 11, 2009
INVENTOR(S) : Wayne P. Young et al.

It is certified that error appears in the above-identified patent and that said Letters Patent is hereby corrected as shown below:

Title Page 2, Section (56) References Cited:
U.S. Patent Documents, line 10 (not including the heading): change "3,757,829" to -- 3,757,629 --; and
U.S. Patent Documents, line 11 (not including the heading): change "Weatherty" to -- Weatherly --.

Title Page 3, Section (56) References Cited:
U.S. Patent Documents, line 20: change "Kloekl" to -- Kloeckl --;
Other Publications, line 1 (not including the heading): change "Mulvlhill" to -- Mulvihill --; and
Other Publications, line 6 (not including the heading): change "Celloscopic" to -- Celioscopic --.

Column 11:
Line 50: after "advancement" insert -- of --; and
Line 67: change "ends of" to -- end of --.

Column 12, line 54:
Change "of opposed" to -- of said opposed --.

Column 13, line 6:
Change "ligations" to -- ligation --.

Column 14, line 12:
Change "said applier" to -- said clip applier --.

Signed and Sealed this

Sixth Day of October, 2009

David J. Kappos
*Director of the United States Patent and Trademark Office*